United States Patent [19]
Ahmed

[11] Patent Number: 5,462,559
[45] Date of Patent: Oct. 31, 1995

[54] ENDOSCOPIC LIGATING INSTRUMENT

[76] Inventor: Munir Ahmed, 501 Haltiwanger, Apt. a-2, Greenwood, S.C. 29649

[21] Appl. No.: 260,380

[22] Filed: Jun. 14, 1994

Related U.S. Application Data

[63] Continuation-in-part of Ser. No. 21,036, Feb. 23, 1993, Pat. No. 5,320,630.

[51] Int. Cl.$^6$ ................................................ A61B 17/00
[52] U.S. Cl. ................................................ 606/140; 606/139
[58] Field of Search ................................ 606/135, 139, 606/140, 141, 165

[56] References Cited

U.S. PATENT DOCUMENTS

| | | | |
|---|---|---|---|
| 5,100,419 | 3/1992 | Ehlers | 606/140 |
| 5,269,789 | 12/1993 | Chin et al. | 606/140 |
| 5,398,844 | 3/1995 | Zaslavsky et al. | 606/140 |

*Primary Examiner*—Tamara L. Graysay
*Assistant Examiner*—Jeffrey A. Schmidt
*Attorney, Agent, or Firm*—Marvin J. Marnock

[57] ABSTRACT

An endoscopic instrument for ligating multiple lesions within a hollow body organ. A flexible endoscope 10 is provided with channels 16–21 for accomodating means for illumination, viewing and application of suction and is also provided with a hollow tubular member 101 affixed to the insertion end of the endoscope. A plurality of cords 103 are laid over the tube 101 to extend longitudinally thereon and be folded over the distal end of the tube. The cords 103 are connected to one another at a common point by a connector 106 inside the tube 101. A plurality of elastic rings 50 are mounted on the tube 101 in stretched condition and overlaying the cords 103. The segment of each cord 103 between each pair of adjacent rings 50 is in slack condition and of a length which equals or exceeds the distance of the tube's distal end to the furthest ring of the pair. By a trip cord 105 threaded through a working channel 19 of the endoscope and connected to the cords 103, a pull can be exerted thereon to simultaneously retract the cords 103 and dislodge each of the rings in controlled stepped sequence in a procedure wherein only one elastic ring at a time moves over the tube in the process of its dislodgement to ligate a lesion which has been suctioned part way into the tube 101.

7 Claims, 9 Drawing Sheets

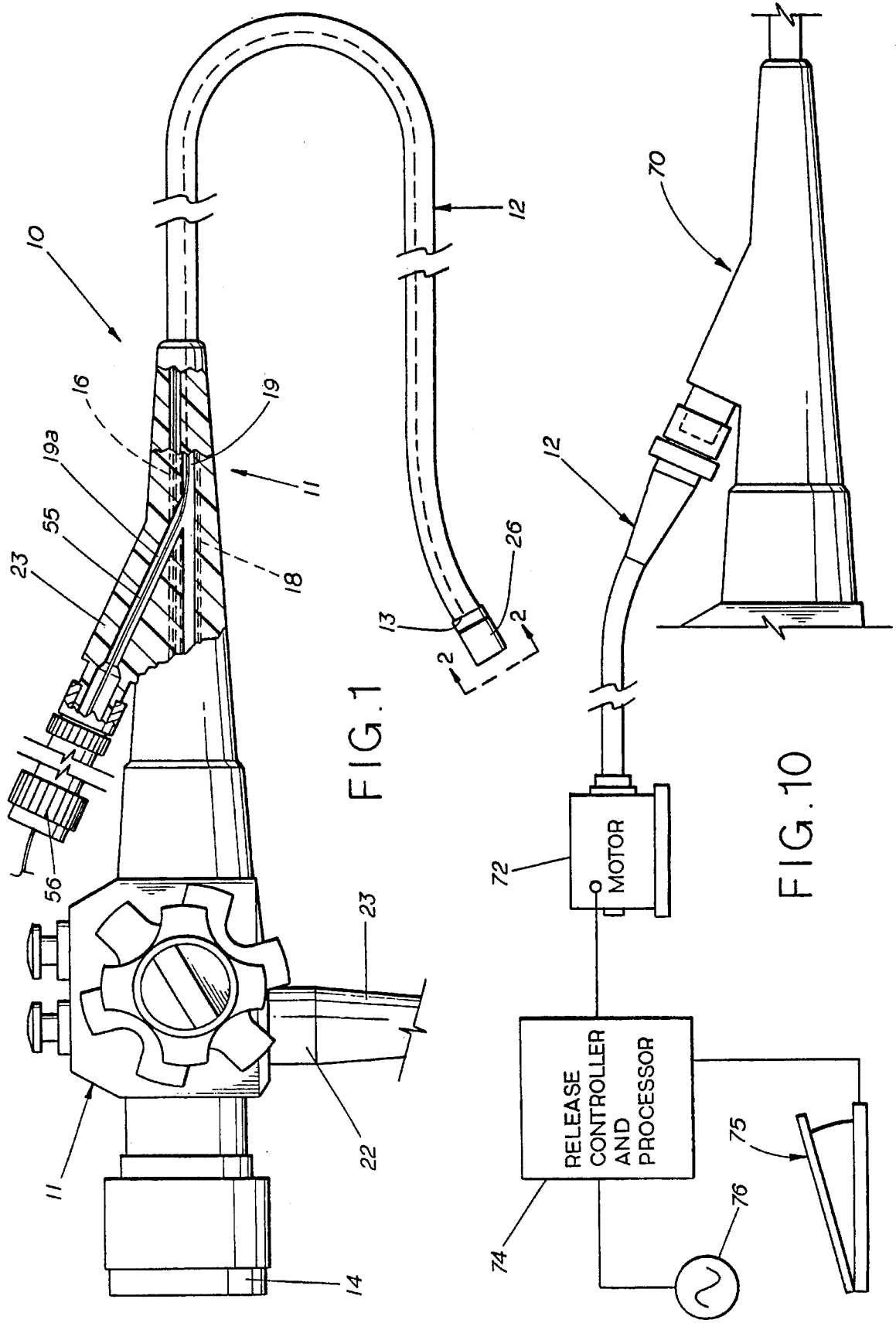

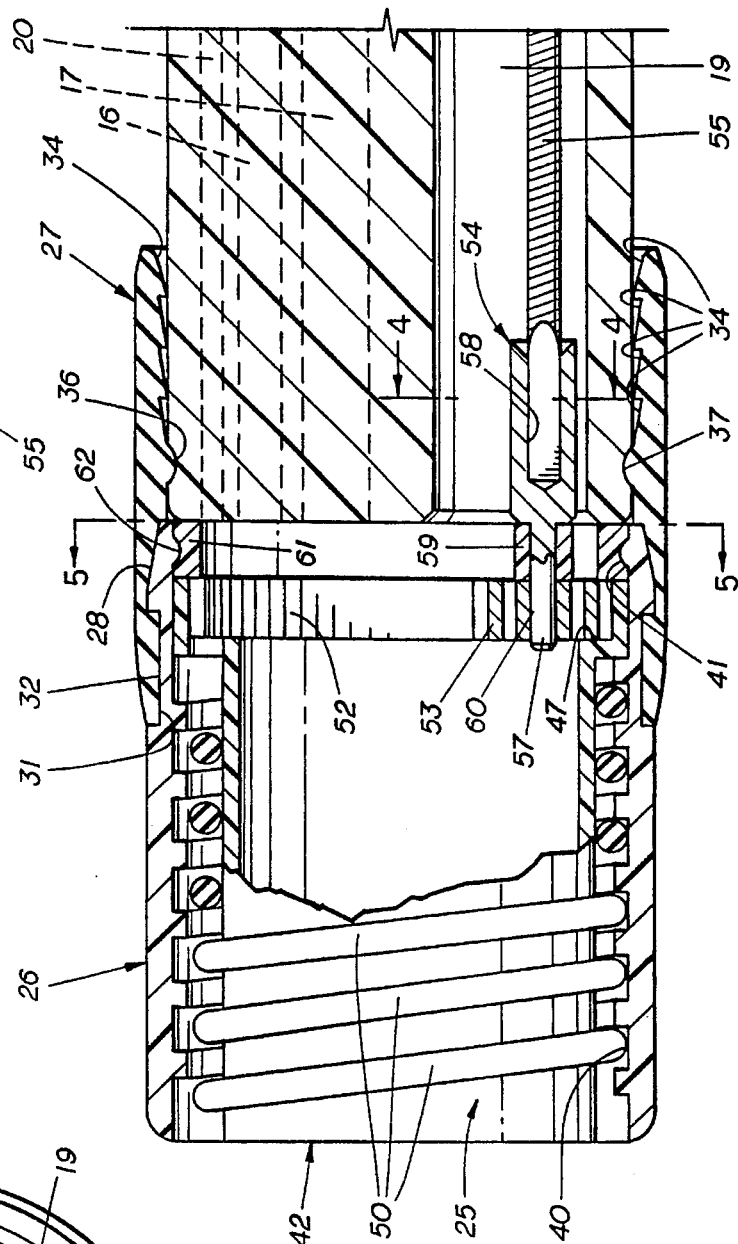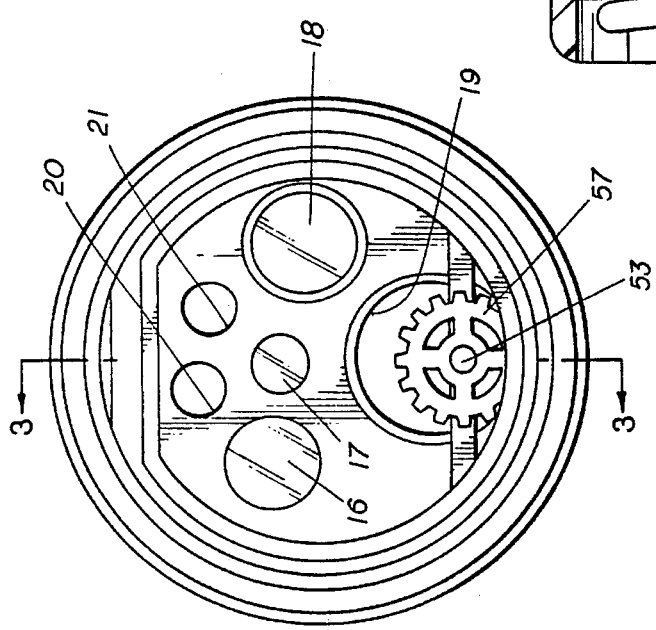

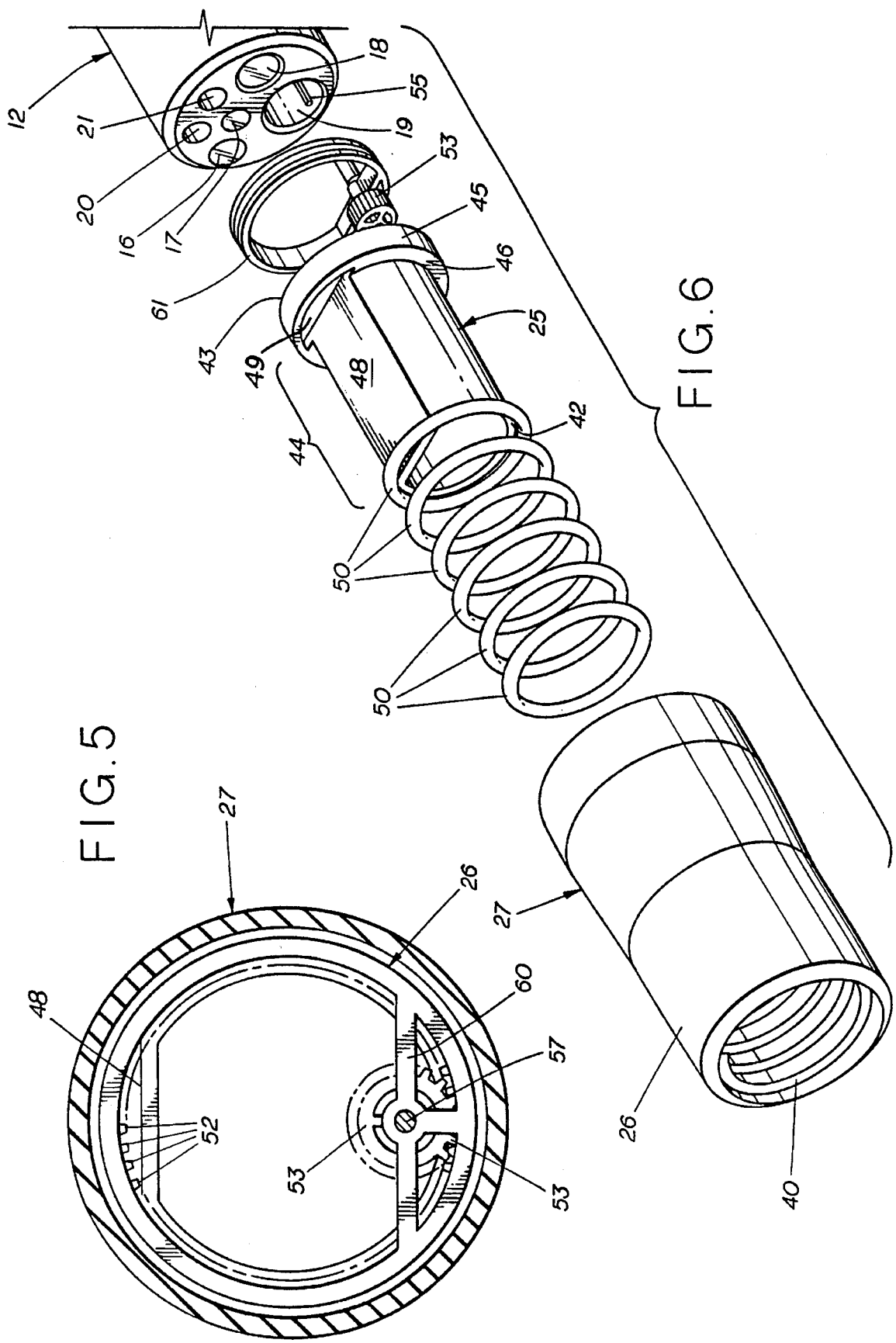

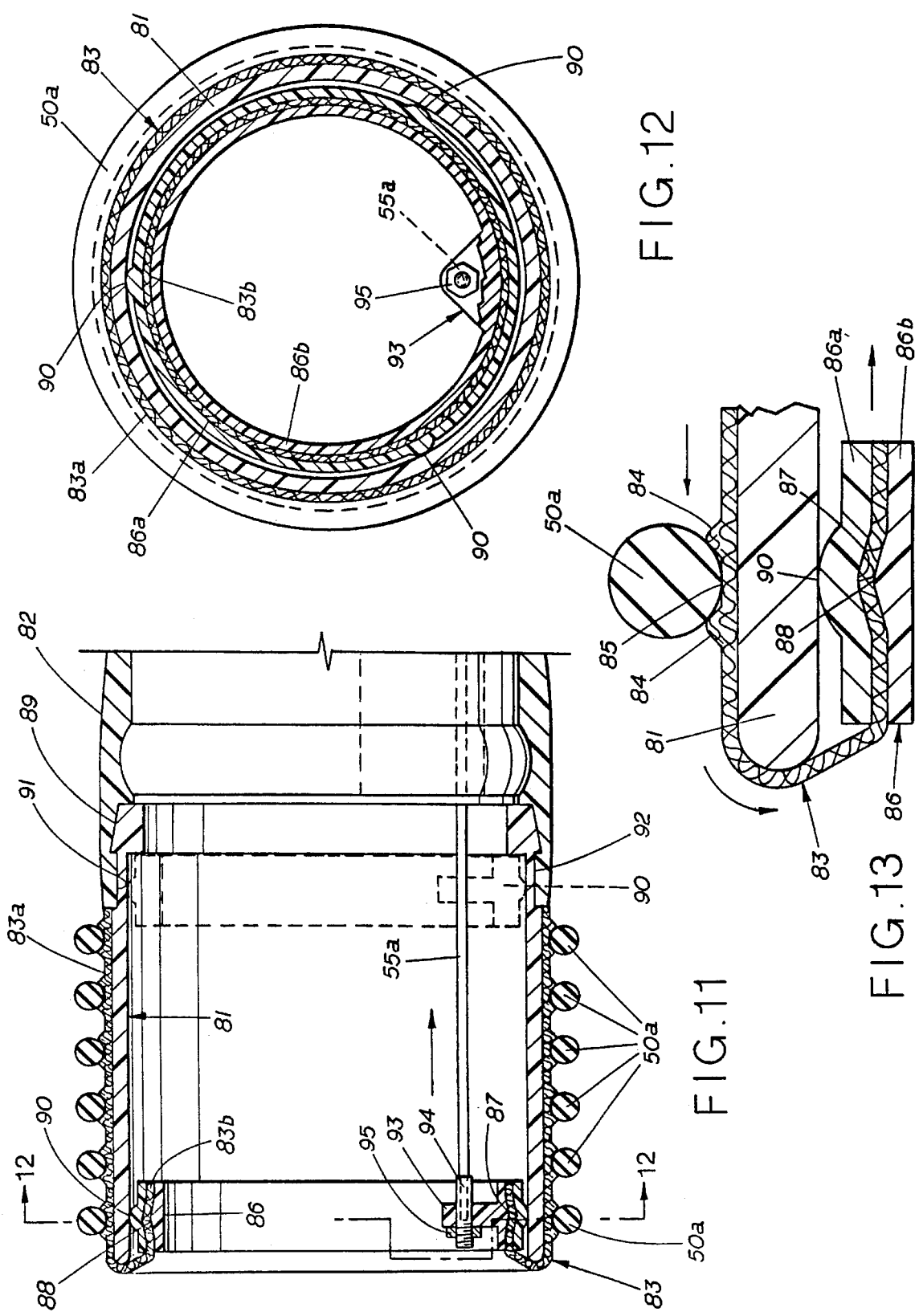

ENDOSCOPIC LIGATING INSTRUMENT

This application is a continuation-in-part of application Ser. No. 08/021036 filed Feb. 23, 1993, now U.S. Pat. No. 5,320,630.

FIELD OF THE INVENTION

The invention relates to an instrument for ligating lesions, and more particularly to an endoscopic instrument for ligating mucosal and submucosal lesions within a hollow organ of the body, such as the alimentary tract.

BACKGROUND ART

The endoscopic treatment of lesions presently encompasses a variety of techniques such as electrocauterization, laser photocoagulation, heat therapy by the application of heat probes, and sclerotherapy which involves the injection of medicine into a target varix by a needle passed through the working channel of the endoscope. A further, widely used and increasingly promising technique involves the ligation of lesions, wherein mucosal and submucosal tissue is strangulated by an elastic ligature.

A variety of instruments for effecting the ligation of body tissue by the application of an elastic ring are well known in the prior art. Some of these instruments, because of their rigidity and size are suited only for treatment of lesions that are in the external regions of the body or in the shallow body cavities. Others are particularly suited for the ligation of tissue in the abdominal cavity, such as for tubal ligation, when the abdominal cavity has been opened surgically.

U.S. Pat. No. 3,760,810 to Van Hoorn discloses an endoscope-equipped instrument comprising a device with two tubes mounted one inside the other, with the inner tube protruding at the front of the outer tube. Means are included to move the outer tube forwardly relative to the inner tube and cause an elastic cord to be dislodged and placed about the tissue to be ligated. In U.S. Pat. No. 4,257,419, there is disclosed an instrument for ligating hemorrhoids wherein a suction tube fitted inside a proctoscope provides means for sucking the hemorrhoid into a suction cavity where a ligating ring is applied. Both of these instruments are rigid devices suited for treating lesions close to the external regions, and both are equipped with only a single elastic ring for treating a single lesion.

There are also instruments in the prior art which employ laparoscope-assisted means for ring ligation such as shown in U.S. Pat. No. 4,257,420 and 4,471,766, wherein the instruments are each equipped with a single elastic band and utilize forceps to position the tissue for ring ligation.

In U.S. Pat. No. 3,870,048, there is disclosed a ring applicator device having forceps slidably mounted in a cylinder for grasping the fallopian tube and including means for displacing an elastic ring to effect a ligation of tissue. While this device can be equipped with a plurality of elastic rings, it's rigidity precludes its use with a flexible endoscope for treating the deeper regions of an internal organ, such as the alimentary tract.

A flexible endoscopic instrument used for ligation purposes and disclosed in U.S. Pat. No. 4,735,194 comprises a flexible fiberoptic endoscope on the end of which is secured an outer tube and an inner tube reciprocally movable therein. A trip wire is fastened to the inner tube to provide rearward motion to the inner tube to cause an elastic ring fitted about the inner tube to slide off and effect ligation. While this instrument is suitable for ligating lesions deep within the alimentary tract, it can only be used to treat but one lesion during a single insertion of the instrument.

In many instances, however, there are a number of lesions present in the organ being treated, such as the esophagus, stomach or colon. If an endoscopic instrument equipped with only one elastic ring is used, the treatment of multiple lesions in the same organ requires the extraction of the endoscope after the placing of each elastic ring about a lesion and reinsertion of the endoscope into the organ to repeat the procedure for placing an elastic ligating ring about each of the lesions. In addition to being time consuming and an associated concern for blood loss when there are bleeding lesions, there are other disadvantages associated with the repetitions of this procedure. The instrument, when withdrawn from the body, is usually covered with blood and mucous. Furthermore, each time the instrument is reinserted into the organ, it becomes necessary to relocate a lesion to be treated and to orient the instrument with respect thereto. In some cases where considerable blood and mucous are present, the relocating of the instrument is a tedious and difficult task.

SUMMARY OF THE INVENTION

A flexible endoscopic instrument is provided with a plurality of elastic ligating rings mounted on one tube of a pair of tubular members which are affixed in coaxial relation to the insertion end of an endoscope. The rings are adapted to be dislodged therefrom in sequence at selectively controlled times for treating multiple lesions during a single insertion of the endoscope into a body organ. The endoscope is equipped with illumination and viewing means to facilitate orientation of the instrument in the body organ, and longitudinally extending tubular passages comprising a channel through which objects may be passed and suction applied for drawing the lesion tissue into the tubular end of the endoscope to facilitate ligation of a lesion, and a working channel through which a flexible actuating cable is inserted. The cable is connected to one of the tubular members and serves as a means for imparting relative motion between the pair of tubular members to sequentially dislodge the elastic rings from the endoscope at controlled times. Each of the elastic rings can be dislodged from the endoscope and placed in ligating relation to a lesion when lesion tissue is drawn into the innermost of the tubular members by a suction force applied through the suction channel and each of the rings can be applied to a different one of the multiple lesions in the body organ during a single insertion of the endoscope.

In one embodiment of the invention, a tubular member is provided with a helical groove in its inner wall and with means at one end for fitting the tubular member onto the insertion end of the endoscope. A plurality of elastic ligating rings are mounted in stretched condition about the periphery of a second tubular member which, when inserted into the first tubular member with a twisting motion, causes the greater part of each of the elastic rings to be placed in a different one of the coils of the helical groove. By a drive gear connection between the flexible cable and the inner tubular member, rotary motion of the cable is imparted to the inner tubular member whereby the elastic rings are adapted to be dislodged one at a time to effect the ligation of multiple lesions during a single insertion of the endoscope.

In a second embodiment, a first rigid tubular member is fitted to the insertion end of the endoscope in coaxial relation thereto. A second tubular member of flexible material is placed on the rigid tubular member with a first outer portion thereof sleeved over the rigid tubular member and a second portion inserted within the first tubular member by folding over the free end of the rigid tubular member. The elastic rings are placed in stretched condition about the outer portion of the flexible tubular member in side-by-side spaced relation to one another. By direct connection of the flexible cable to the inner second portion of the flexible tubular member, the cable can be retracted to pull most of the outer sleeve portion over the free end of the rigid tube and into the interior of the rigid tubular member thereby causing the elastic rings to be dislodged from the endoscope one at a time as they pass over the end of the rigid tubular member at times controlled by the retraction of the flexible cable.

In a third embodiment, a rigid tubular member is fitted to the insertion end of the endoscope and a plurality of cords connected together at the same point inside the tube, are each folded over its distal end with the free end portion thereof extending in the longitudinal direction of the tube and angularly spaced relative to one another with respect to the axis of the tube. A plurality of elastic rings are placed in stretched condition about the tube at longitudinally spaced locations thereon and also over the cords which lay over the tube. Each cord is provided with knots at predetermined spaced locations thereon against each of which an elastic ring is placed. By means of a trip wire or trip line threaded through a working channel of the endoscope and connecting to the cords at this mutual connecting point, the cords can be simultaneously retracted to pull the rings over the distal end of the tube in controlled sequence. By also providing a slack length of the cord between each pair of adjacent elastic rings, which slack length equals or exceeds the distance of the tube's distal end to the furthermost ring of the pair, a small pulling force is required to dislodge a ring from the tube.

BRIEF DESCRIPTION OF THE DRAWINGS

FIG. 1 is a longitudinal view, partly in section, of an endoscopic ligating instrument representing a preferred embodiment of the invention;

FIG. 2 is a frontal plan view of the insertion end of the endoscopic ligating instrument of FIG. 1:

FIG. 3 is a section view through the end portion of the instrument as taken along the section line 3—3 in FIG. 2;

FIG. 4 is a fragmentary view in cross section showing details of the end portion of the flexible actuating cable at its connection with a planetary gear in a tubular member in an assembly of tubular members affixed to the insertion end of the endoscope;

FIG. 5 is a section view through the insertion end of the endoscope as taken along the section line 5—5 in FIG. 3;

FIG. 6 is an exploded view of a tubular assembly which is affixed to the insertion end of the endoscope;

FIG. 10 is a block plan view showing an endoscopic instrument as shown in FIG. 1 which is provided with a step-motor for selectively and automatically controlling the rotation of the flexible cable;

FIG. 11 is a fragmentary view in longitudinal cross-section of a modified form of tubular assembly which is connectable to the insertion end of the endoscope of the invention;

FIG. 12 is a sectional view as taken along the section line 12—12 in FIG. 11;

FIG. 13 is an enlarged fragmentary view of the tubular assembly of FIG. 11 which shows the nature and direction of the relative movement which is imposed between the paired tubular members of the assembly for effecting the discharge of an elastic ligating ring;

DETAILED DESCRIPTION OF THE INVENTION

Figure 7:
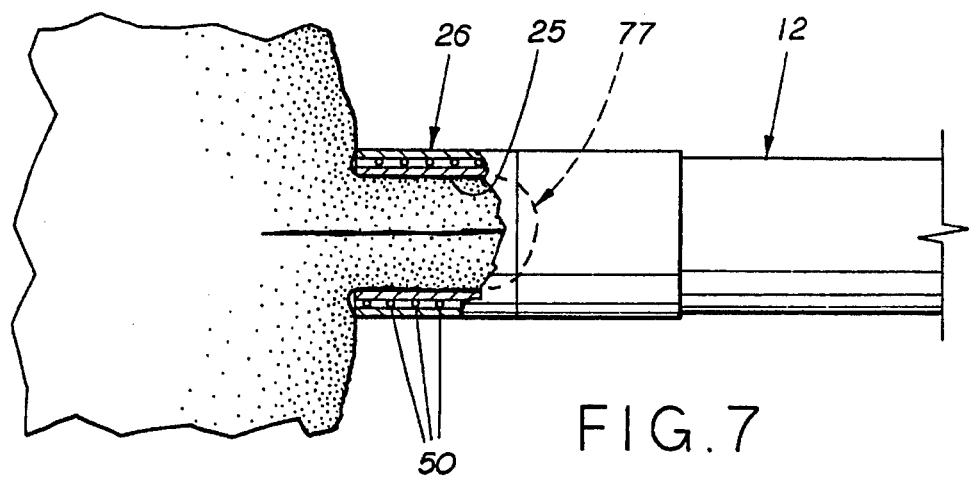
FIG. 7 is a fragmentary view, partly in section, showing the insertion end of the instrument of the invention applied to a lesion with lesion tissue drawn by suction into an inner tubular member on the end of the instrument.

Referring more particularly to the drawings, there is shown in FIG. 1 a flexible endoscopic instrument 10 of a length which permits access to the deeper regions of a hollow body organ, such as the alimentary tract. The instrument 10 comprises a conventional endoscope with an operating controls section 11 of rigid construction and a flexible section 12 which extends therefrom and is of a length sufficient to reach the deeper regions of the alimentary tract. The distal end of the flexible section 12 is the insertion end 13 of the endoscope and the viewing end 14 of the endoscope is at the end of the rigid operating controls section 11 remote from the end thereof which connects to the flexible section 12.

The endoscope is provided with passages 16–21 which extend longitudinally therein from its insertion end 13 to exit ports near the viewing end 14 of the endoscope. The passages comprise an illumination channel 16 through which is inserted a fiber optic cable for the transmission of light from a light source, a viewing channel 17 which is also provided with a fiber optic cable for viewing purposes, and a channel through which objects may be passed or suction applied 18. The illumination channel and suction channel exit laterally through a lateral extension 22 of the side wall of the endoscope at a location on the operating controls section 11 near the viewing end 14. At their exit location, the fiber optic cable from channel 16 and the channel 18 are connectable through an umbilical cable 23 to a control device (not shown) which is adaptable for supplying illumination to the transmission optic cable and for connecting the channel 18 to an appropriate means for applying a suction therethrough. The fiber optic viewing channel 17 extends to the viewing end 14 of the endoscope which may be provided with a viewing lens and an adapter for mounting a camera thereon, if desired.

The endoscope is also provided with a working channel 19 which extends through the endoscope from its insertion end 11 to an exit in the lateral extension 22. The working channel 19 includes a branch 19a which extends through an angularly extending protuberance 24 to a second exit near the viewing end of the endoscope.

Additional channels 20 and 21, shown in FIG. 2, may be utilized for delivering pressurized air or a jet stream of water for cleaning the lens.

In the embodiment of the invention shown in FIGS. 1 through 6, the insertion end of the endoscope is fitted with an assembly of coaxially arranged tubes 25, 26, the outer tube 26 of which is secured in coaxial relation thereto preferably by a tubular adapter 27 which provides a friction fit as shown in FIG. 3 although other fastening means such as a threaded connection might be suitably employed. The tube 26 is preferably of transparent plastic material for enhancing the illumination and field of vision from the insertion end of the endoscope, although other inert material might also be suitable including stainless steel. The tube 26 is provided at its attaching end with an external frusto-conical bevel surface 28 to facilitate the placement of the tubular adapter 27 thereover. The adapter 27 is preferably of a flexible material such as plastic and is provided with an internal diameter which allows it to be sleeved tightly over the tube 26. For further enhancing the connection, the adapter 27 is provided with an internal annular flange 31 which is adapted to seat in an accommodating annular groove 32 formed externally about the surface of the tube 26, thereby locking the adapter 27 to the tube 26.

At its other end, the inner wall of the adapter 27 is formed with a succession of outwardly diverging frusto-conical grooved surfaces 34 which provide teeth-like edges for enhancing its grip on the endoscope when sleeved over the end thereof. In addition, it is provided with an internal annular latching flange 36 which is adapted to seat in a latching groove 37 formed about the exterior of the endoscope.

The inner wall of outer tube 26 is formed with a helical groove 40 which extends from its distal end for the greater part of its length. Near its attaching end, the inner wall of outer tube 26 is formed with an internal annular flange 41.

The inner tubular member 25 has a forward end 42 and a rearward end 43 and comprises a first elongate section 44 and an adjoining shorter section 45 of circular cylinder configuration and larger radial dimensions. The tubular member 25 has an external annular shoulder 46 formed at the junction of the elongate tubular section 44 with the larger diameter section 45. The tubular member 25 is also provided an internal annular radial shoulder 47, which is formed at the junction of the bore of section 45 with the smaller bore of the elongate section 44.

The elongate section 44 has a radial cross section in the configuration of a segmented circle and an external cylindrical surface characterized by an elongate planar surface section 48 which extends from the forward end 42 of the tubular member 25 to the radial shoulder 46.

The inner tubular member 25 serves as a carrier for a plurality of elastic ligating rings 50 which are placed in stretched condition about the elongate section 44 and mounted thereon in side-by-side relation to one another and in sleeved relation to the section 44. The elastic rings 50 are typically of rubber material or an inert non-toxic plastic composition.

The tubular member 25 is also provided with a circular planetary gear 52 which is seated in the bore of the circular section 45 in the coaxial relation therewith. The gear 52 may be fabricated as an integral part of the tubular member 25 or it could be separately formed and bonded to the radial shoulder 47 and the inner cylindrical wall of circular section 45 by an appropriate adhesive although other fastening means could also be used. An opening 49 is also provided in the radial shoulder 47 to insure full communication of the interiors of the tubular members 25 and 26 with the suction channel 18.

When completely assembled as shown in FIG. 3, the gear teeth of planetary gear 52 are in meshing engagement with a drive gear 53 which is mounted by a connecting adapter 54 on the end of a flexible steel cable 55, preferably a single wire, which is inserted through the working channel 19 of the endoscope. The cable 55 extends through the working channel section 19a where it is fitted with a rotary control means such as a knob 56 for manually effecting axial rotation of the cable 55.

The adapter 54 comprises a shaft 57 enlarged at one end which is provided with a socket 58 characterized by a socket cavity of rectangular transverse cross section which receives the squared end of the cable 55. At its other end, the shaft 57 is journalled for rotation on a transverse support 60 fitted internally of tube 25. The shaft 57 is also fitted with a drive gear 53 which is fixed on the shaft 57 in coaxial relation thereto by a press fit or any suitable bonding means. Also sleeved about the shaft 57 is a plastic spacer 59 which is in abutting engagement with the drive gear 53 and one end of the socket 58.

Also shown in FIG. 3, a retaining ring 61 is also fitted into the end of the inner tubular member 25 in coaxial relation therewith and in abutting engagement with both the rearward end of the tubular member 25 and the planetary gear 52. The retaining ring 61 is provided in its outer surface with a circumferential groove 62 which receives the annular flange 41 of the tubular member 25 and latches the retaining ring 61 in position.

In assembly of the instrument 10 the elastic ligating rings 50 must be placed onto the inner tubular member 25 before it is inserted in the outer tubular member 26. This is also done before the tubular members 25, 26 are fitted onto the endoscope. The elastic ligating rings 50, when in the relaxed state are of a diameter less than that of the insertion end of the endoscope, which for representative endoscopes, is in the range of approximately 9 mm. to 13 mm. The rings 50 are placed in stretched condition onto the elongate section 44 of the tubular member 25 in side-by-side relation to one another and in sleeved relation to the section 44. The tubular member 25 is then inserted with an axially twisting motion through the attaching end of the outer tubular member 26 whereby each elastic ring, except for the portion thereof which rests atop the planar surface of the inner tubular member 25, is placed in a coil of the helical groove 40 in spaced relation to the adjacent elastic ring in the next adjacent coil of the helical groove.

The tubular assembly, comprising tubular member 25 and 26 with tubular adapter 27 secured to the member 26, is then sleeved onto the insertion end of the endoscope such that the planetary gear 52 and drive gear 53 are in meshed driving engagement with one another and the attaching end of the tubular member 26 abuts the insertion end of the endoscope.

When treating a patient, the endoscopic instrument of the invention is first inserted into the affected organ, such as the alimentary tract, to place the insertion end of the endoscope in the vicinity of lesions in the alimentary tract. In some instances, however, it may be preferred that insertion of the instrument be preceded by the insertion of an endoscopic overtube (not shown) into the alimentary tract and the instrument then be inserted through the overtube. In either case, the instrument is then oriented for sighting of a target lesion, such as lesion 77 shown in FIG. 7, and the instrument advanced under the control of a human operator until the distal end of the tubular member 25 contacts the lesion area and is placed in surrounding relation to the target lesion.

Figure 8:
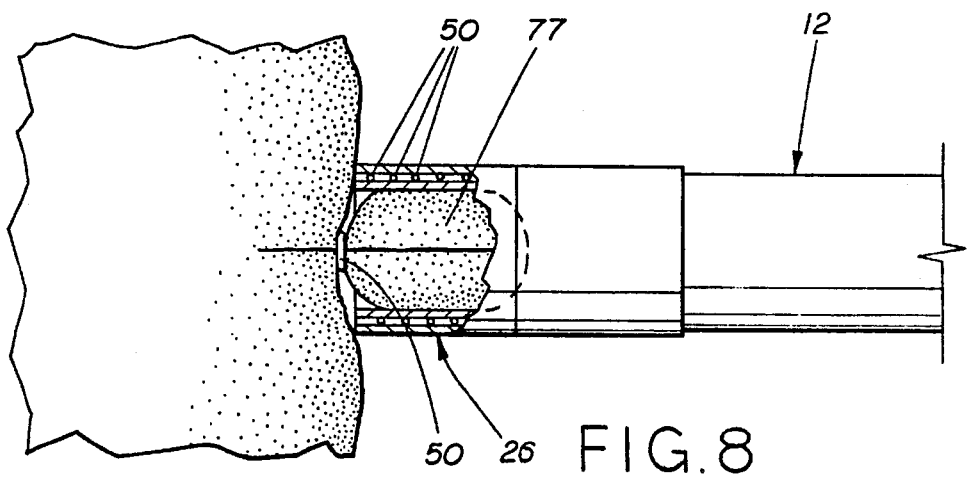
FIG. 8 is a view similar to FIG. 7 but showing an elastic ligating ring applied about a lesion after its dislodgement from the end of the endoscopic instrument of the invention.
Figure 9:
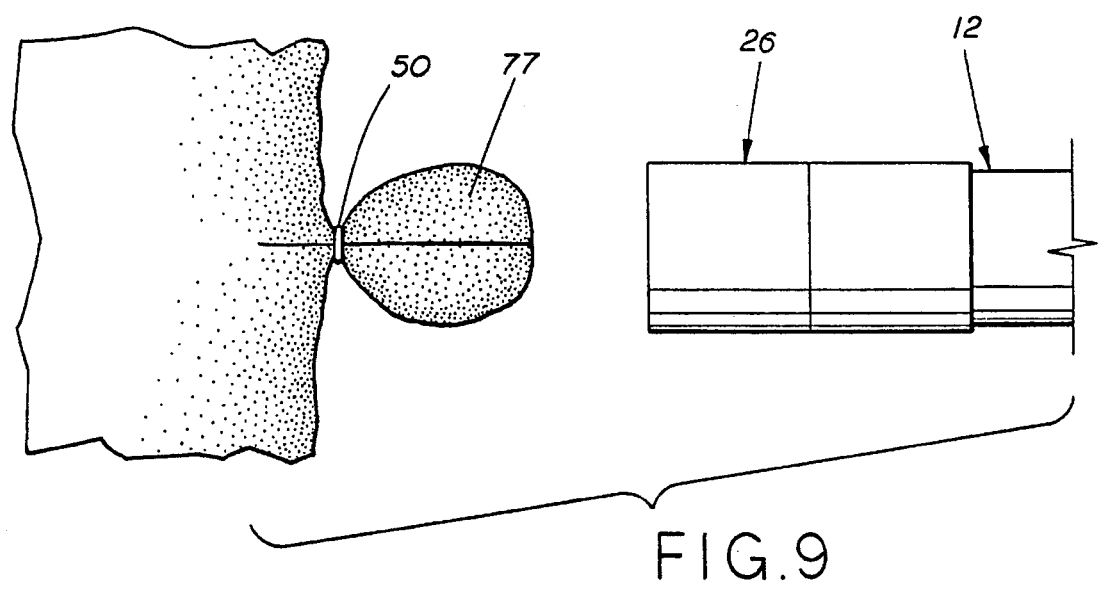
FIG. 9 shows a lesion with an elastic ligating ring applied in strangulating relationship hereto.

A suction force is then applied through the suction channel 18 to completely draw the lesion tissue into the inner tubular member 25 as shown in FIG. 7. The operator then manually initiates axial rotation of the cable 55 and the inner tubular member 25 in the spirally forward direction of the helical groove 40 whereby the elastic rings 50 are driven along the surface of the tubular member 25 by the walls of the helical groove 40 until one of the elastic rings is dislodged from the instrument and placed in ligating relation about the base of the target lesion as shown in FIG. 8. The end of the instrument 10 is then withdrawn from around the lesion tissue, as shown in FIG. 9.

It is to be appreciated that by continuing the axial rotation of the tubular member 25, more of the elastic rings can be dislodged from the instrument. Accordingly, the endoscopic instrument of the invention permits the successive ligation of multiple lesions during a single insertion of the instrument. With patients who are not bleeding, the ligation treatment is started at the most distal point in the alimentary tract and then continued proximally so that elastic bands which are placed about lesion tissue are not disturbed by movement of the instrument. The instrument therefore facilitates the treatment of multiple lesions and alleviates the need for repeated removal and reinsertion of the instrument and reloading of an elastic ring for treating each lesion.

In some instances, particularly where vision is obscured, the instrument operator may have difficulty in ascertaining the precise amount of rotation of the flexible cable 55 that is necessary for dislodging one and only one elastic ring 50 when ligating a single target lesion. In this respect, a modified form of the invention, which enables the axial rotation of the cable 55 in steps of precise amounts, is represented by the endoscopic instrument 70 as shown in schematic form in FIG. 10. The instrument 70 is identical in all respects to the instrument 10 except for the means of imparting axial rotation to the flexible cable 55 and identical components are identically numbered. In lieu of a knob 56 which enables the manual rotation of the cable 55, the instrument 70 is provided with automatic means represented by a stepping motor 72 and a controller 74 for rotation of the cable 55 in precisely controlled amounts. The controller 74 and motor 72 are connected to receive power from an electrical power source 76. A foot pedal trigger switch 75 is used by the operator to energize the stepping motor 72 for a precise time interval during which time the flexible cable 55 is axially rotated by an amount which moves the elastic rings a precise distance along the tubular member 25 such that the most distal elastic ring 50 is forced off the end of the tubular member 25 and the remaining rings 50 are retained thereon. In effect, the precise time interval of motor operation moves the elastic rings a distance which corresponds to the distance between adjacent coils of the helical groove 40.

It is to be appreciated therefore that the endoscopic instrument 70 provides the operator with means for precisely controlling when an elastic ring 50 is dislodged from the instrument and for insuring that only one elastic ring is dislodged when ligating a target lesion. It is therefore possible for the operator to dislodge additional elastic rings in sequence and at times controlled by the operator so that multiple lesions can be ligated during a single insertion of the instrument.

A further embodiment of the invention represented by the endoscopic instrument 80 is disclosed in FIGS. 11 through 15. The endoscopic instrument 80 differs from the instruments 10 and 70 in the nature and operation of the tubular assembly which is affixed to the insertion end of the endoscope, but is otherwise identical thereto. As shown in FIG. 11, a rigid tube 81 is fixed in coaxial relation to the insertion end of the endoscope, preferably by a sleeve adapter 82. A tubular textile member 83 of an inelastic material, such as the commercial product Kevlar or other inelastic flexible material, is mounted onto the rigid tube 81 such that the member 83 is folded over the distal end of the tube 81 with a first portion 83a thereof being sleeved over the tube 81 and a second portion 83b thereof disposed internally of the tube 81 and substantially coaxial thereto.

As shown in FIG. 11, a plurality of elastic ligating rings 50a are placed in stretched condition in encircling relation about the portion 83a of the tubular member 83. The textile material of portion 83a is provided with an external surface having a plurality of annular ridges 84 in the encircling relation thereto and preferably arranged in pairs which define a plurality of uniformly spaced annular recesses or grooves 85, each of which is adapted to receive an elastic ring 50a therein. The elastic rings 50a are therefore maintained in uniform side-by-side spacing on the tubular portion 83a.

The end of the second portion 83b of the textile tubular member 83 is fitted with a rigid annular ring clamping assembly 86 to which the textile fabric of the tubular member 83 is attached. The clamping assembly 86 comprises an outer retaining ring 86a and an inner clamping ring 86b which is of a smaller external diameter than the internal diameter of the outer ring 86a and is insertable therein from the distal end of the tube 81 to clamp the portion 83b of the textile tubular member 83 therebetween. Preferably, the inner wall of the outer ring 86a is formed with an annular coaxial groove 87 and the outer wall of the inner ring 86b is formed with an annular ridge 88 of conforming configuration and location such as to serve in retaining the textile member 83 therebetween. The outer ring 86a is also provided with at least three centering protuberances 90 which are in uniform angular spacing and serve to maintain the ring 86a in coaxial relation to the tube 81 and in a tight friction fit therein.

As best seen in FIG. 11, the adapter 82 is sleeved over an annular bevel surface 89 on the attaching end of the tube 81 and is provided with an internal annular flange 91 which latches in an annular groove 92 formed about the external surface of the rigid tube 81. At its other end, the adapter is designed for a press fit connection with the insertion end of the endoscope as provided for the adapter 27 in the embodiment of FIG. 1 or could be provided with threads, if desired.

A flexible cable 55a, similar to the cable 55 shown in the embodiment of FIG. 1, and similarly threaded through the working channel of the endoscope is attached to an internal flange 93 on the inner wall of the clamping ring 86b. As best seen in FIGS. 11 and 12, one end of the cable 55a is placed in an axial blind bore formed inwardly from one end of a sleeve member 94 which is swaged in engagement therewith. The sleeve member 94 which is externally threaded at its other end, is inserted through an opening in the flange 93 and secured by a nut 95 on its threaded end. It is thus to be seen that by a pull on the cable 55a to the right as shown in FIG. 11, the portion 83b of textile tubular member 83 which is interior of the rigid tube 81 is increased and the portion 83a which is exterior of the tube 81 is decreased.

The relative movement of the flexible tube 83 with respect to the rigid tube 81 is illustrated by arrows in FIG. 13 which show the textile tubular member 83 sliding over the distal end of the tube 81. As this movement increases, the most distal of the elastic ligating rings 50a passes over the distal end of the tube 81 and is discharged therefrom. When the assembly of tubes 81, 83 are placed in surrounding relation to a target lesion, and lesion tissue is drawn into the tube 83 by suction in a manner as previously described, it is to be appreciated that ligation of a lesion as shown in FIG. 9 can be readily achieved.

It is important that only a single ligating ring 50a be discharged from the instrument 80 for treating each lesion and the movement of the cable 50a must be determined accordingly. After treating one lesion, the instrument can be reoriented in surrounding relation to another lesion and the procedure repeated. Accordingly, multiple lesions can be ligated during a single insertion of the instrument. For most applications, the instrument should be provided with at least six elastic rings 50a.

Figure 15:
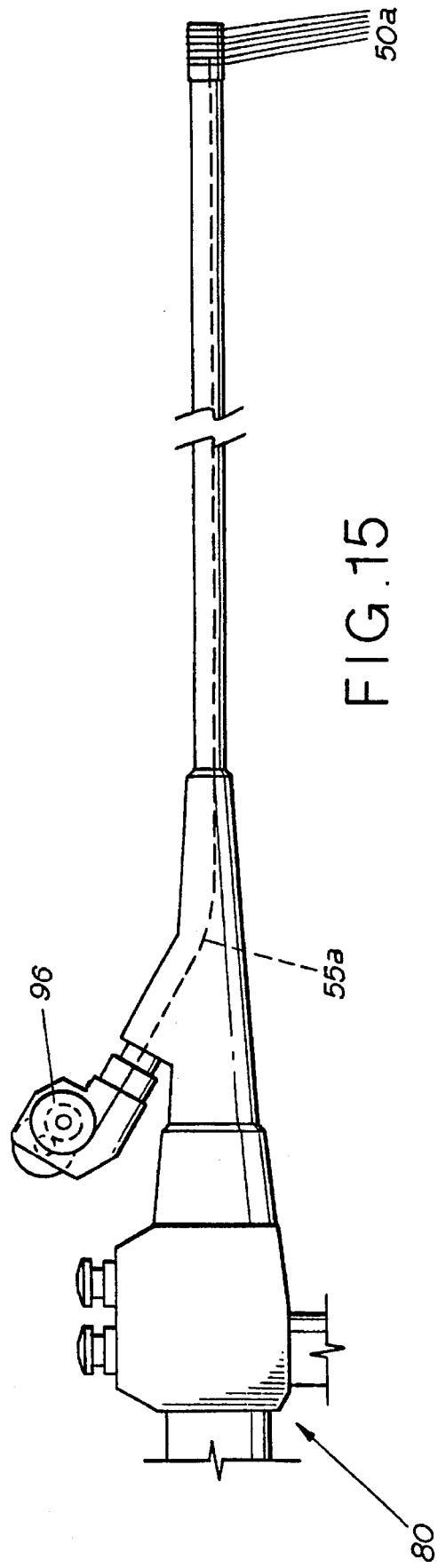
FIG. 15 is a plan view of an embodiment of the invention as illustrated in FIGS. 11 through 14.

In FIG. 15, the cable 55a is shown attached to a reel 96 whereby an indexed rotation thereof is designed to move the cable 55a a predetermined distance to cause the discharge of only a single ligating ring 50a. Obviously, the movement could be controlled manually or other techniques employed for controlling a precise axial movement of the cable 55a.

Figure 14:
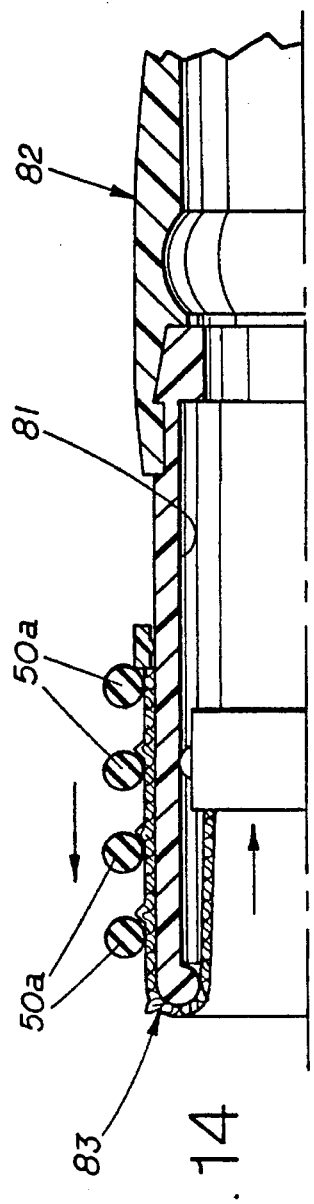
FIG. 14 is a view similar to FIG. 13 but showing a modified form of ribbing which is provided on the exterior of a textile member of the tubular assembly of FIG. 11.

A variation in the arrangement of ridges 84 on the external surface of the textile tubular member 83 is shown in FIG. 14. In this modified form of the member 83, only a single ridge 84 is used for aligning the elastic rings 50a in uniform spacing on the member 83. The rings 50a are installed whereby each is in abutting engagement with the side of a ridge 84 which faces toward the distal end of the tubular assembly so as to prevent their being moved or disturbed as the instrument is inserted into a body organ.

It is to be noted that in the embodiment of the invention disclosed in FIGS. 11 through 15, the force required to pull the sleeve member 83 over the distal end of the tube 81 increases proportionately with the number of elastic rings, such that a strong and sturdy construction must be used for the parts mounted on the insertion end of the endoscope and the component parts for imparting sliding movement between the sleeve 83 and the tube 81 and for a precise amount of sliding to ensure that only one ring is dislodged at a time. The force to dislodge the first ring, which must be strong enough to pull the sleeve and all the elastic rings towards the distal end of the tube, is considerably greater than the force required to dislodge the last remaining elastic ring from the tube.

Figure 16:
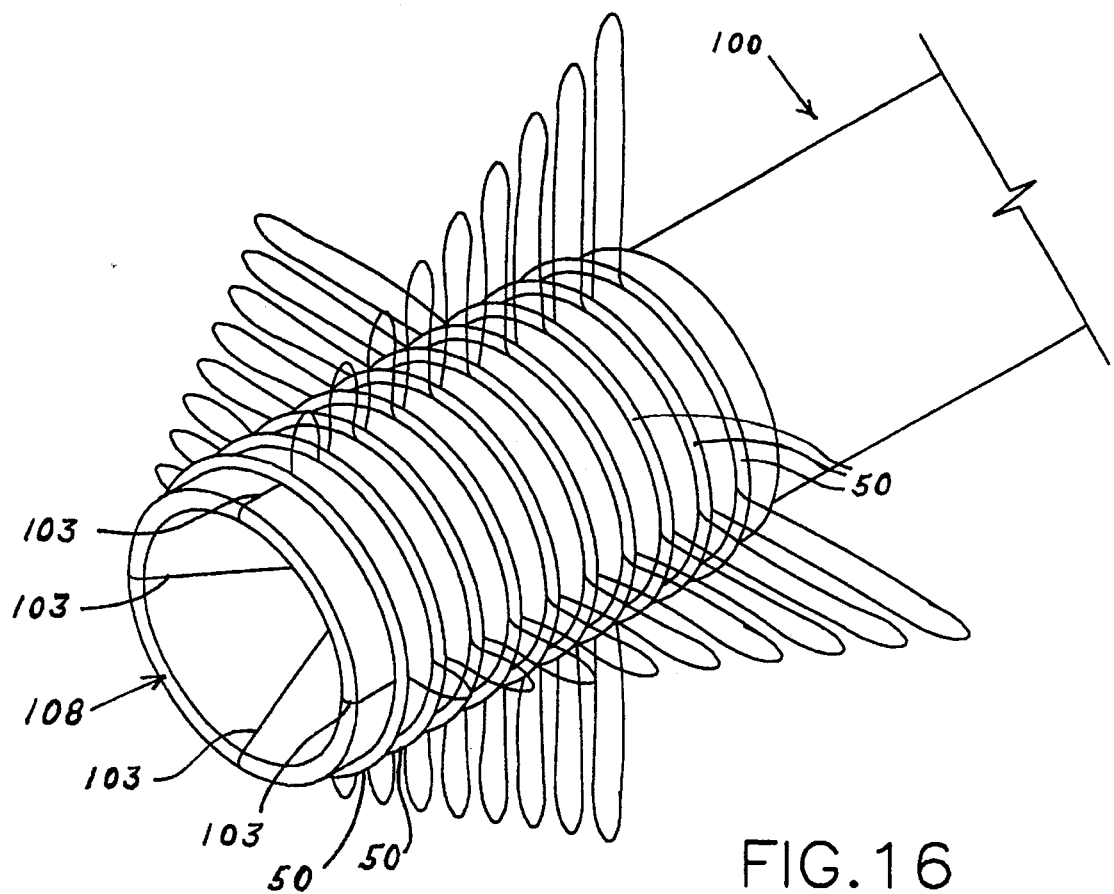
FIG. 16 is a perspective fragmentary view of a further embodiment of the invention showing the insertion end of an endoscope with elastic rings displaceably mounted on a rigid tube affixed thereto.

A third embodiment of the invention represented by the endoscopic instrument 100 disclosed in FIGS. 16 through 19 requires a pulling force to dislodge an elastic ring which is comparable to that required for dislodging the last ring of the sleeve version disclosed in FIGS. 11 through 15. As best seen in FIG. 16, a transparent rigid tube 101 is fitted to the insertion end of the endoscope 100 by an adapter section 102 which provides a friction fit with the insertion end of the endoscope. The endoscope 100 is provided with a plurality of flexible and substantially elastic cords 103, each of which is folded over the distal end of the tube 101 and includes a first portion which is laid over the exterior surface of the tube and a second portion which is disposed internally of the tube. The ends of the cords 103 inside the tube are fastened to one end of a flexible line 105 as by tying thereto or the use of an adapter connector 106. From its connection with cords 103, the flexible line 105 is threaded through the working channel 19 of the endoscope and exits near the rearward end of the endoscope such that the exiting end portion of the line 105 may be fitted with a handle.

Figure 17:
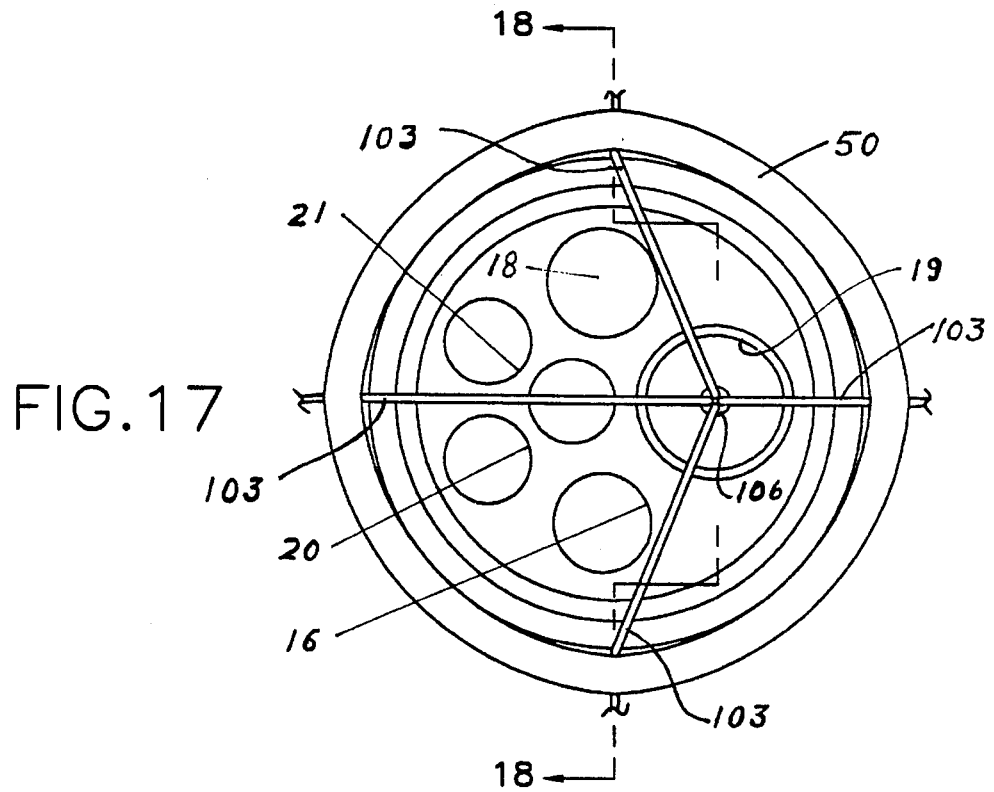
FIG. 17 is a front view of the apparatus attached to the insertion end of the endoscope of FIG. 16.

As best seen in FIG. 17, the cords 103 are disposed in preferably uniform angular spacing about the longitudinal axis 107 of the tube 101. A plurality of elastic ligating rings 50 are each placed in stretched condition in sleeved relationship about the tube 101 and in overlying relation to the plurality of cords 103 to thereby hold the cords against the tube 101.

Figure 18:
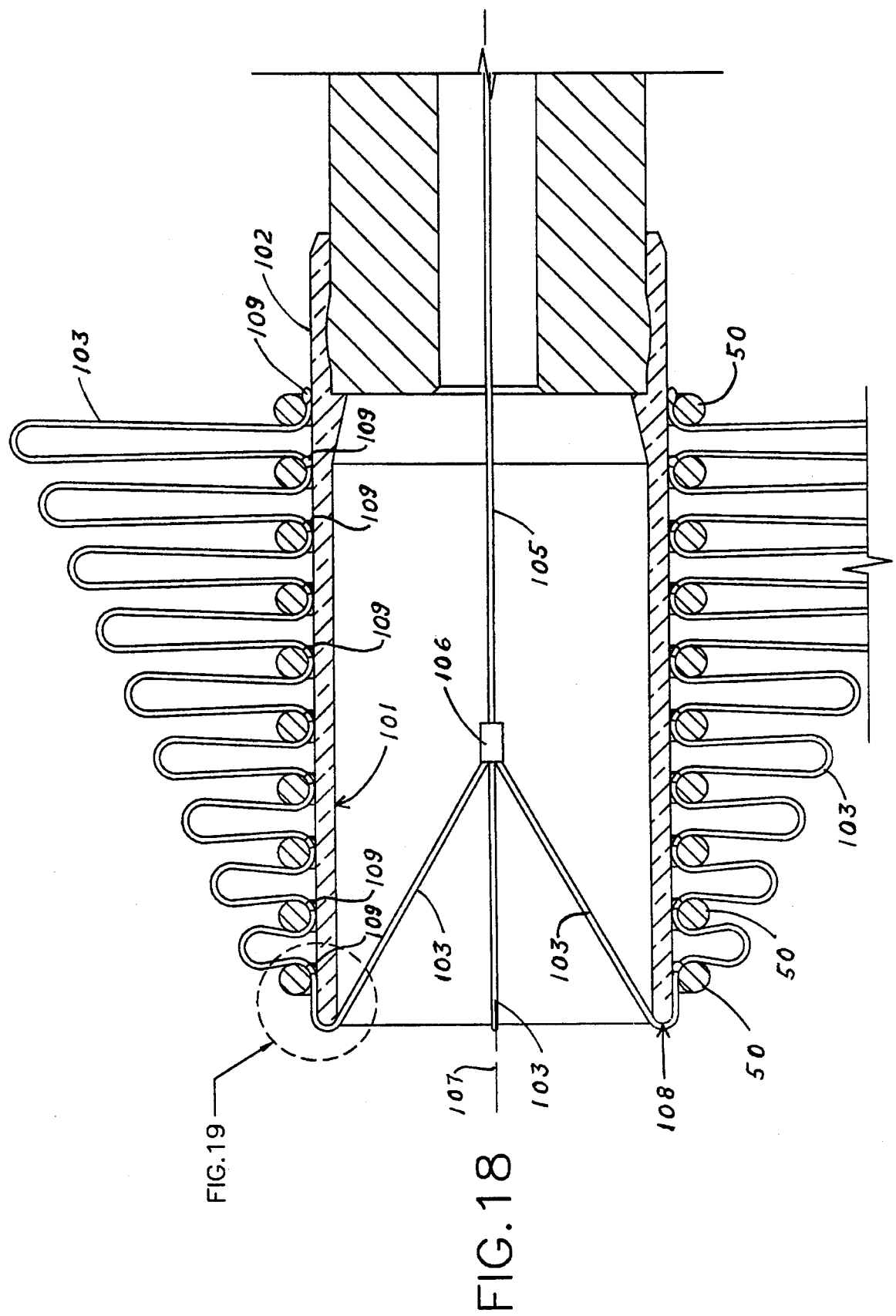
FIG. 18 is a longitudinal sectional view of the endoscope apparatus as taken along the section line 18—18 in FIG. 17 showing the arrangement of elastic rings on the rigid tube connected to the end of the endoscope.
Figure 19:
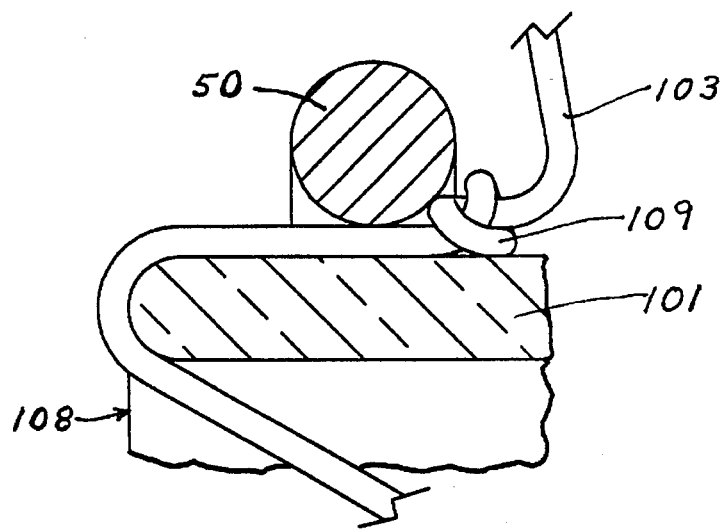
FIG. 19 is an enlarged fragmentary view showing the distal end of the tubular member fitted to the end of the endoscope in FIG. 16.
Figure 20:
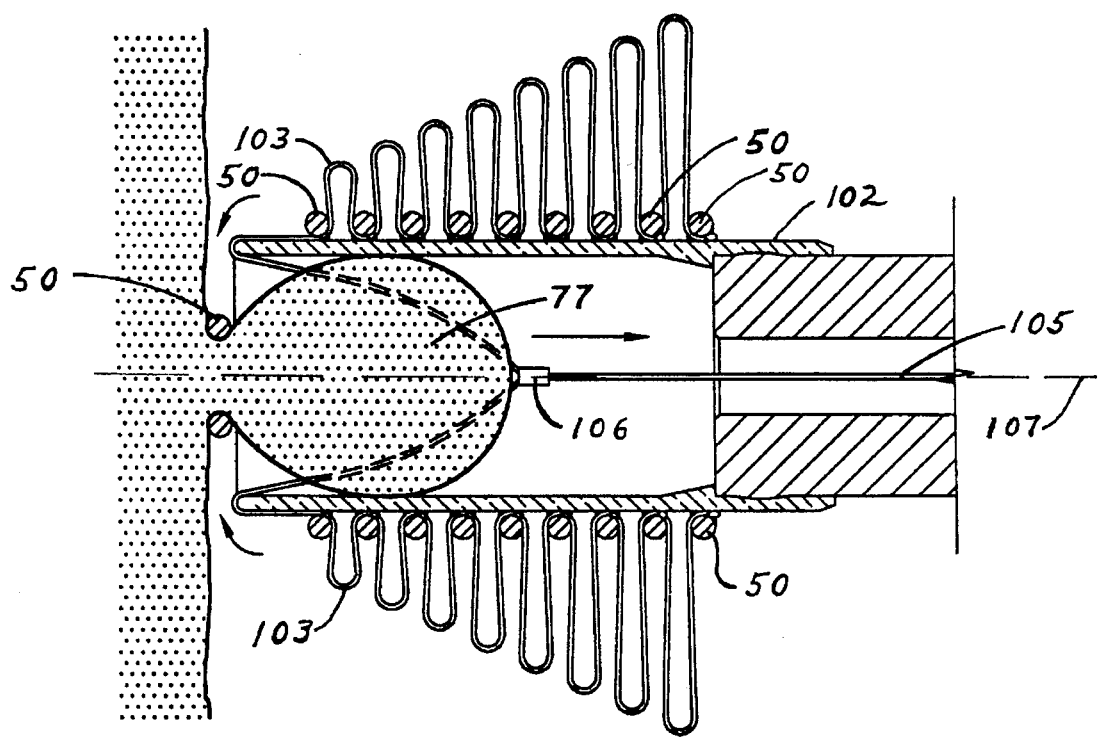
FIG. 20 is a longitudinal sectional view similar to FIG. 18 but showing a suctioned lesion ligated by an elastic ring which has been dislodged from the tube.

It is to be noted in FIGS. 16, 18 and 20 that the rings 50 are spaced from one another in the longitudinal direction of the tubular member at successsingly greater distances from the distal end 108. Each cord 103 is also provided with a series of longitudinally spaced knots 109 against each of which an elastic ring 50 is placed on the forward side of the knot. A means for imparting sliding motion between said cords and the tubular member is provided by the flexible line element 105 by which because of its connection to the ends of the cords 103 within the tubular member 101, a pulling force may be exerted at its outer end to cause sliding movement between the cords and the tubular member so as to dislodge each of the elastic rings in desirably controlled sequence. When the pull is applied, a knot 109 acts as a shoulder which precludes relative movement between the elastic ring and the cord until the ring is dislodged at the distal end of the tubular member.

As is best shown in FIG. 16, each cord 103 includes a segment of cord between each pair of adjacent elastic rings which is in slack condition and of a length which is equal to the distance between said pair plus the distance from the distal end of the tube 101 to the ring of the pair which is nearest the distal end 108. It will therefore be seen that when the cords are pulled a distance which moves the forward ring of the pair to the distal end of the tube and off the tube, the slack length of cord suffices to preclude any movement of the remaining elastic rings. It is therefore to be noted that the required pulling force to dislodge a ring is that which is necessary to move a single ring and the required force does not increase as additional rings are dislodged.

After the cords 103 and elastic rings 50 have been loaded on the rigid tube 101 and positioned thereon as shown in FIGS. 16 and 18, it may be a desirable option to place a flexible sleeve of plastic or a textile materal to fit loosely over the cords 103 and the tube 101. Such a sleeve, when attached at one end to the flexible section 12 of the endoscope and extending over the cords 103 and elastic rings 50 to approximately the distal end of the tube 101, would serve to protect against "snagging" of the slack segments or loop of cords between the rings when the endoscope is in use or prepared for use.

It is to be understood that the foregoing descriptions of a preferred embodiment of the invention has been presented for purposes of illustration and explanation and are not intended to limit the invention to the precise forms disclosed. For example, a motor control could be provided for controlling the movement of the cable 55a in precise steps. Also, the number of elastic ligating rings 50 or 50a could be greater or less than those illustrated herein. In some instances the rings 50a can be aligned on the textile tubular member 83 without ridges 84. It is to be appreciated therefore, that various material and structural changes may be made by those skilled in the art without departing from the spirit of the invention.

I claim:

1. A flexible endoscopic instrument for ligating a multiplicity of lesions within a hollow body organ, such as the alimentary tract, said instrument comprising:

(a) a flexible fiber optic endoscope having a forward insertion end and a rearward end, said endoscope including means for illumination and viewing through said endoscope, means for providing a suction force at said insertion end, and a working channel;

(b) a tubular member having a forward distal end, a rearward end and a longitudinal axis, said rearward end having means for providing attachment to the insertion end of the endoscope;

(c) a plurality of string-like cords of flexible substantially inelastic material, each said cord being folded over the distal end of the tubular member with a first portion of each said cord overlaying a part of the exterior of said tubular member and a second portion thereof being disposed internally of said tubular member, said cords being oriented in angular spacing about the longitudinal axis of said tubular member;

(d) a plurality of elastic ligating rings removably mounted in stretched condition on said tubular member in coaxial relation thereto and each of said rings being in overlying contacting relation to all of said plurality of cords, said rings being spaced from one another in the longitudinal direction of the tubular member at successively greater different distances from the distal end of the tubular member; and (e) means for imparting relative sliding motion between said cords and said tubular member to dislodge each of the elastic rings in controlled sequence during a single insertion of the endoscope into the body organ whereby each of the elastic rings can be dislodged from the endoscope and placed in ligating relation to a lesion when lesion tissue is drawn into the tubular member by said suction means with each ring being applied to a different one of multiple lesions present in the body organ, said means for imparting relative sliding motion comprising a flexible line element threaded through the working channel of the endoscope and connecting at one end to said cords disposed within said tubular member and exiting the endoscope at the rearward end thereof whereby a pulling force may be exerted on the other end of the line element to cause sliding movement of the cords over said tubular member, each said cord being arranged in slack condition between each pair of adjacent elastic rings.

2. A flexible endoscopic instrument for ligating a multiplicity of lesions within a hollow body organ, such as the alimentary tract, said instrument comprising:

(a) a flexible fiber optic endoscope having a forward insertion end and a rearward end, said endoscope including means for illumination and viewing through said endoscope, means for providing a suction force at said insertion end, and a working channel;

(b) a tubular member having a forward distal end, a rearward end and a longitudinal axis, said rearward end having means for providing attachment to the insertion end of the endoscope;

(c) a plurality of string-like cords of flexible substantially inelastic material, each said cord being folded over the distal end of the tubular member with a first portion of each said cord overlaying a part of the exterior of said tubular member and a second portion thereof being disposed internally of said tubular member, said cords being oriented in angular spacing about the longitudinal axis of said tubular member;

(d) a plurality of elastic ligating rings removably mounted in stretched condition on said tubular member in coaxial relation thereto and in overlying relation to said cords, said rings being spaced from one another in the longitudinal direction of the tubular member and between at least one pair of adjacent elastic rings each of said cords having a slack segment of cord of a length which is at least equal to the distance between the distal end of the tubular member and the ring of said pair which is furthest from said distal end; and (e) means for imparting relative sliding motion between said cords and said tubular member to dislodge each of the elastic rings in controlled sequence during a single insertion of the endoscope into the body organ whereby each of the elastic rings can be dislodged from the endoscope and placed in ligating relation to a lesion when lesion tissue is drawn into the tubular member by said suction means with each ring being applied to a different one of multiple lesions present in the body organ, said means for imparting relative sliding motion comprising a flexible line element threaded through the working channel of the endoscope and connecting at one end to said cords disposed within said tubular member and exiting the endoscope at the rearward end thereof whereby a pulling force may be exerted on the other end of the line element to cause sliding movement of the cords over said tubular member, each said cord being arranged in slack condition between each pair of adjacent elastic rings.

3. An endoscopic ligating instrument as set forth in claim 2 wherein each said cord on the portion thereof which overlies said rigid tubular member includes a series of shoulders at spaced intervals and against each of which a different one of said elastic rings is placed in abutting engagement and facing the distal end of said rigid tubular member and wherein each of said shoulders of a cord is in substantially co-planar relationship with a shoulder of each of the other cords.

4. An endoscopic ligating instrument as set forth in claim 2 wherein each said cord on the portion thereof which overlies said rigid tubular member includes a series of knots at spaced intervals and against each of which a different one of said elastic rings is placed in abutting engagement and facing the distal end of said rigid tubular member and wherein each of said knots of a cord is in substantially co-planar relationship with a knot of each of the other of said cords.

5. A flexible endoscopic instrument for ligating a multiplicity of lesions within a hollow body organ, such as the alimentary tract, said instrument comprising:

(a) a flexible fiber optic endoscope having a forward insertion end and a rearward end, said endoscope including means for illumination and viewing through said endoscope, means for providing a suction force at said insertion end, and a working channel;

(b) a tubular member having a forward distal end, a rearward end and a longitudinal axis, said rearward end having means for providing attachment to the insertion end of the endoscope;

(c) a plurality of string-like cords of flexible substantially inelastic material, each said cord being folded over the distal end of the tubular member with a first portion of each said cord overlaying a part of the exterior of said tubular member and a second portion thereof being disposed internally of said tubular member, said cords being oriented in angular spacing about the longitudinal axis of said tubular member;

(d) a plurality of elastic ligating rings removably mounted in stretched condition on said tubular member in coaxial relation thereto and in overlying relation to said cords, said rings being spaced from one another in the longitudinal direction of the tubular member at successively greater different distances from the distal end of the tubular member, such that the length of each cord between each pair of adjacent elastic rings is at least equal to the distance between the distal end of the tubular member and the furthest ring of said pair from said distal end; and (e) means for imparting relative sliding motion between said cords and said tubular member to dislodge each of the elastic rings in controlled sequence during a single insertion of the endoscope into the body organ whereby each of the elastic rings can be dislodged from the endoscope and placed in ligating relation to a lesion when lesion tissue is drawn into the tubular member by said suction means with each ring being applied to a different one of multiple lesions present in the body organ, said means for imparting relative sliding motion comprising a flexible line element threaded through the working channel of the endoscope and connecting at one end to said cords disposed within said tubular member and exiting the endoscope at the rearward end thereof whereby a pulling force may be exerted on the other end of the line element to cause sliding movement of the cords over said tubular member, each said cord being arranged in slack condition between each pair of adjacent elastic rings.

6. An endoscopic ligating instrument as set forth in claim 5 wherein each said cord on the portion thereof which overlies said rigid tubular member includes a series of radially extending shoulders at spaced intervals and against each of which a different one of said elastic rings is placed in abutting engagement and facing the distal end of said rigid tubular member and wherein each of said shoulders of a cord is in substantially co-planar relationship with a shoulder of each of the other cords.

7. An endoscopic ligating instrument as set forth in claim 5 wherein each said cord on the portion thereof which overlies said rigid tubular member includes a series of knots at spaced intervals and against each of which a different one of said elastic rings is placed in abutting engagement and facing the distal end of said rigid tubular member and wherein each of said knots of a cord is in substantially co-planar relationship with a knot of each of the other of said cords.

* * * * *